US011253390B2

(12) United States Patent
Fallon et al.

(10) Patent No.: US 11,253,390 B2
(45) Date of Patent: Feb. 22, 2022

(54) IMPRESSION TRAY WITH INTEGRAL HANDLE FOR AN ORAL JAW ADVANCEMENT APPLIANCE

(71) Applicants: James S Fallon, Laguna Niguel, CA (US); Richard Jung, Laguna Niguel, CA (US)

(72) Inventors: James S Fallon, Laguna Niguel, CA (US); Richard Jung, Laguna Niguel, CA (US)

( * ) Notice: Subject to any disclaimer, the term of this patent is extended or adjusted under 35 U.S.C. 154(b) by 581 days.

(21) Appl. No.: 15/984,124

(22) Filed: May 18, 2018

(65) Prior Publication Data
US 2019/0350748 A1    Nov. 21, 2019

(51) Int. Cl.
*A61F 5/56*    (2006.01)

(52) U.S. Cl.
CPC ................... *A61F 5/566* (2013.01)

(58) Field of Classification Search
CPC ...... A61F 5/56; A61F 5/566; A61F 2005/563; A61C 7/08; A61C 7/36; A61C 9/0006
See application file for complete search history.

(56) References Cited

U.S. PATENT DOCUMENTS

| 3,692,025 | A | * | 9/1972 | Greenberg | ........... A63B 71/085 128/857 |
| 5,320,114 | A | * | 6/1994 | Kittelsen | .............. A61C 17/036 128/861 |
| 5,720,302 | A | * | 2/1998 | Belfer | ..................... A61F 5/566 128/848 |
| 5,816,255 | A | * | 10/1998 | Fishman | ............. A61C 9/0006 128/861 |
| 8,833,374 | B2 | | 9/2014 | Fallon et al. | |
| 9,622,837 | B2 | | 4/2017 | Jansheski | |

FOREIGN PATENT DOCUMENTS

WO    WO 97/32537    *    3/1997

* cited by examiner

*Primary Examiner* — Camtu T Nguyen
(74) *Attorney, Agent, or Firm* — Morland C. Fischer

(57) ABSTRACT

Disclosed herein is an impression tray to be removably attached to an oral jaw advancement appliance that is worn over the teeth of a user during sleep to reduce the effects of snoring and sleep apnea. The impression tray has a handle with a first end affixed to a curved rear impression forming stop and an opposite free end that is pushed through the oral appliance so as to extend outwardly from the front thereof. The curved rear impression forming stop of the handle is held flush against the rear of the appliance, and a curved front impression forming stop is detachably connected to the opposite free end of the handle and slidable therealong to lie flush against the front of the appliance. The handle of the impression tray permits the oral appliance to be lowered into and lifted out of boiled water so that an accurate impression of the user's teeth can be made therein.

6 Claims, 3 Drawing Sheets

IMPRESSION TRAY WITH INTEGRAL HANDLE FOR AN ORAL JAW ADVANCEMENT APPLIANCE

BACKGROUND OF THE INVENTION

1. Field of the Invention

This invention relates to an impression tray that is removably attached to an oral jaw advancement appliance of the kind that is worn in the mouth and over the teeth of a user to help maintain an open air path to the user's throat by which to reduce the effects of snoring and sleep apnea. The impression tray includes an integral handle that enables the oral appliance to be lowered into and lifted out of a pot of boiled water and, after being cooled, positioned in the user's mouth so that an accurate impression of the user's upper and lower sets of teeth can be made in the appliance.

2. Background Art

U.S. Pat. No. 8,833,374 issued Sep. 16, 2014 and entitled INTRA-ORAL MANDIBULAR ADVANCEMENT APPLIANCE describes a unique oral appliance to be inserted in the mouth and worn over the teeth of a user to maintain an open airway through the appliance and to the user's throat to thereby improve the user's breathing during sleep. The patented appliance has particular application for use by those wishing to reduce the effects of snoring and/or sleep apnea. The appliance includes upper and lower tray assemblies against which the user's upper and lower sets of teeth are seated during use. The lower tray assembly is slidably adjustable relative to the upper tray assembly to correspondingly and selectively adjust the position of the user's lower jaw relative to his upper jaw in order to keep the aforementioned airway open as the user's condition changes over time.

The upper and lower tray assemblies of the patented oral jaw advancement appliance include relatively soft upper and lower bite impression channels in which impressions of the user's upper and lower sets of teeth are made to ensure that the appliance will reliably adhere to the user's teeth during sleep. To accomplish the foregoing, the oral appliance is initially dipped into a pot of boiled water to soften the upper and lower bite impression channels. After the oral appliance is removed from the boiled water, it is cooled so that the user can then bite into the impression channels to create the impressions therein of his teeth.

A tool must first be located and then coupled to the oral jaw advancement appliance so that it can be safely dipped into and held in the boiled water. Once it has been heated, the user will sometimes grip the oral appliance with a set of tongs. Because the tongs are typically made from metal, the user may burn his fingers. In other cases, the tongs have been known to damage and/or deform the oral appliance. In still other cases, even when safely heated, it is sometimes difficult for the user to accurately position the oral appliance in his mouth so that a reliable impression of his teeth can be made therein.

Accordingly, what would be desirable is an impression tool that is adapted to be removably attached to either the aforementioned patented oral jaw advancement appliance or a similar oral appliance so that the appliance can be safely dipped into and lifted out of a pot of boiled water and then accurately positioned in the user's mouth to enable the user to center his bite into the appliance and thereby make a reliable impression therein of his upper and lower sets of teeth.

SUMMARY OF THE INVENTION

Disclosed herein is an impression tray that has an integral handle and is adapted to be removably attached to an oral jaw advancement appliance having a curved shape so as to be worn in the mouth and over the teeth of a user during sleep to reduce the effects of snoring and sleep apnea. The oral appliance may be conventional and includes flexible upper and lower tray assemblies which are engaged by the user's upper and lower sets of teeth during sleep. Each of the upper and lower tray assemblies includes a relatively soft and impressionable bite impression channel against which the user's teeth are pressed and a relatively hard chassis over which each bite impression channel is molded. The user advances the position of the lower tray assembly relative to the upper tray assembly so that his lower jaw will be correspondingly repositioned relative to his upper jaw to maintain an open airway through the oral appliance to the user's throat while sleeping.

The impression tray to be removably attached to the oral jaw advancement appliance includes an elongated flexible handle. Affixed to a first end of the handle is a rear impression forming stop that has a curved configuration to match the shape of the rear of the oral appliance. A pair of spaced parallel aligned compression slots run axially along the handle. A position locking bump is formed at and extends outwardly from each side of the handle.

The handle of the impression tray is initially subjected to lateral squeezing forces so as to be compressed at the compression slots thereof to enable the opposite free end of the handle to be pushed through an airflow passage of the oral appliance located between the upper and lower tray assemblies thereof. The free end of the handle continues to move through the oral appliance until the curved rear impression forming stop that is affixed to the first end of the handle lies flush against the rear of the appliance and the free end of the handle extends outwardly from the front of the appliance. At this time, the squeezing forces are terminated and the handle expands such that the position control bumps of the handle snap into locking engagement with the front of the oral appliance.

A curved front impression forming stop is now pushed along and detachably connected to the outwardly extending free end of the handle of the impression tray until the front impression forming stop lies flush against the front of the oral appliance at which it is held in place by the position control bumps of the handle. The outwardly extending free end of the handle is now gripped by the user so that the oral jaw advancement appliance being carried by the impression tray can be dipped into and removed from a pot of boiled water. Once the oral appliance is removed from the boiled water and cooled, it can then be accurately positioned in the user's mouth by means of the handle so that the user can bite against the bite impression channels of the appliance to form therein an accurate impression of his upper and lower sets of teeth.

DESCRIPTION OF THE PREFERRED EMBODIMENT

Figure 1:
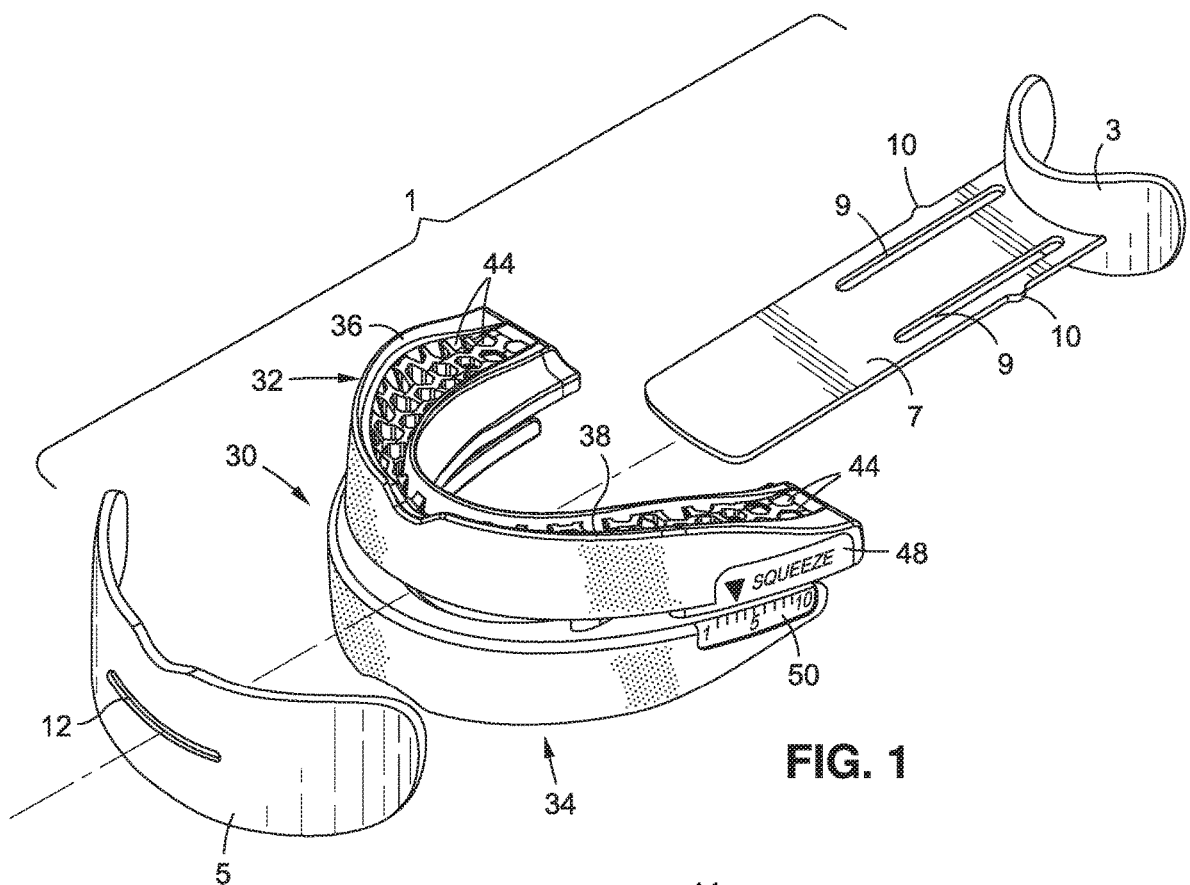
FIG. 1 is an exploded perspective view of a preferred impression tray with an integral handle to be removably attached to an oral jaw advancement appliance.
Figure 2:
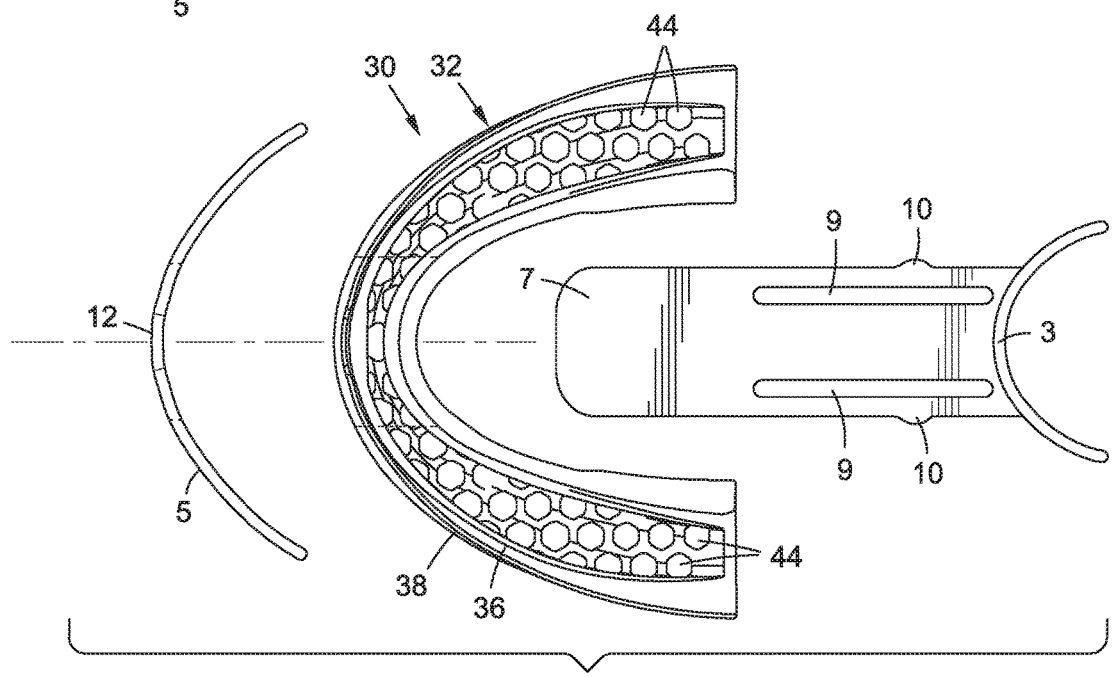
FIG. 2 is a top exploded view of the impression tray with integral handle and the oral jaw advancement appliance shown in FIG. 1.
Figure 3:
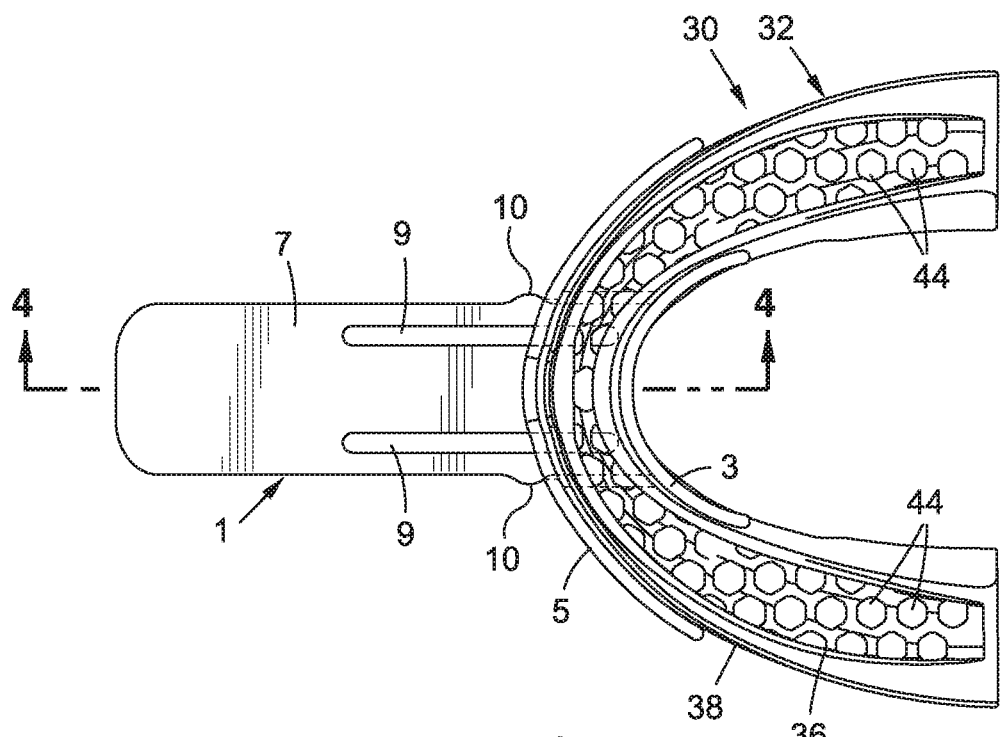
FIG. 3 shows the impression tray of FIGS. 1 and 2 removably attached to the oral jaw advancement appliance.
Figure 4:
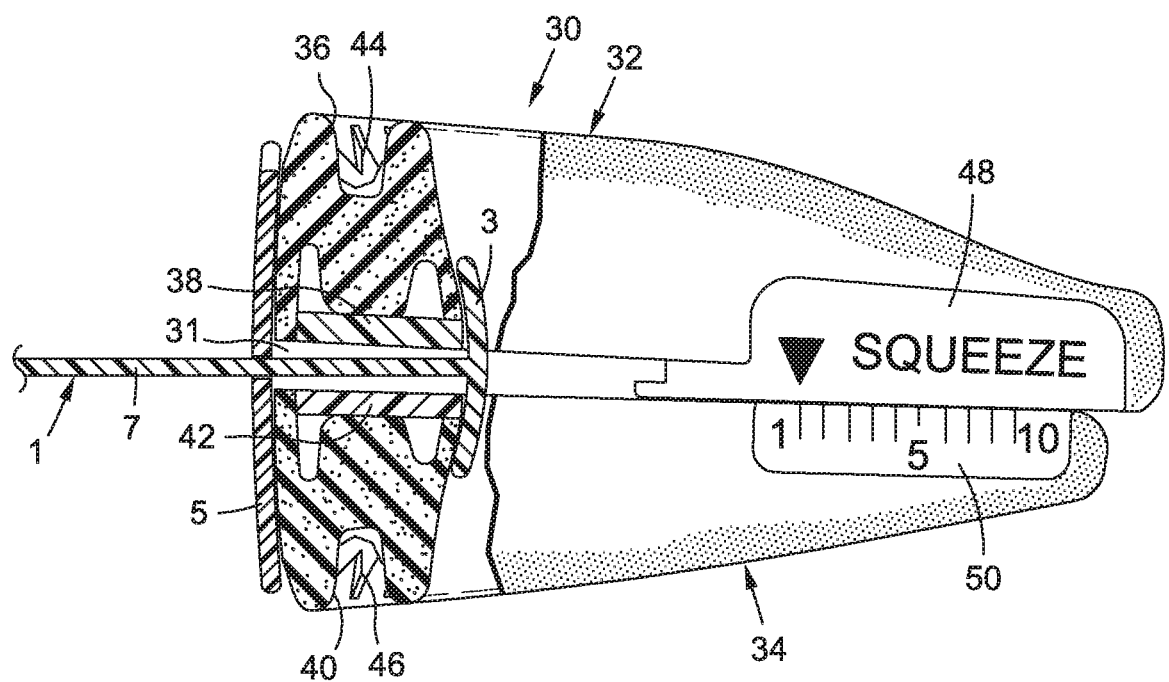
FIG. 4 is a cross-section of the impression tray and oral jaw advancement appliance taken along lines 4-4 of FIG. 3.

Referring to the drawings, details are provided of a unique impression tray 1 that has particular application to be used for heating and customizing the shape of an oral jaw advancement appliance of the kind that is sized to fit within the mouth and over the teeth of a user during sleep in order to reduce the effects of snoring and/or sleep apnea. The oral appliance with which the impression tray 1 will be used may be one that is known. In this regard, it is to be understood that the particular oral appliance with which the impression tray 1 is used should not be considered as a limitation of this invention.

By way of example only, one oral jaw advancement appliance 30 that is suitable to be with the impression tray 1 is that is shown in FIGS. 1-4 of the drawings. Reference may be made to patent application Ser. No. 15/229,715 filed Aug. 5, 2016 for a detailed description of the oral appliance 30 shown in FIGS. 1-4. The aforementioned description of oral appliance 30 is therefore incorporated herein by reference, and only a partial description thereof will be provided herein.

The oral appliance 30 enables the user to selectively and controllably position his lower jaw relative to his upper jaw to maintain a continuous airflow passage 31 (best shown in FIG. 4) through the appliance to the user's throat during sleep by which to reduce the effects of snoring and sleep apnea. The oral appliance 30 includes a curved and flexible upper tray assembly 32 and a curved and flexible lower tray assembly 34 that are spaced one above the other so as to create the aforementioned airflow passage 31 therebetween. The upper and lower tray assemblies 32 and 34 are slidably coupled to one another such that the lower tray assembly 34 can be moved back and forth by the user relative to upper tray assembly 32. In particular, a forward displacement of the lower tray assembly 34 results in a forward displacement of the user's lower jaw relative to his upper jaw to enable the size of the air path to the user's throat to be regulated.

The upper tray assembly 32 of the oral jaw advancement appliance 30 includes an upper bite impression channel 36 and an upper chassis 38 that are molded together so that the upper bite impression channel 36 lies on and is surrounded by the upper chassis 38. Both the upper bite impression channel 36 and upper chassis 38 have a generally arcuate (i.e., curved) configuration to match the bite pattern of the teeth carried by the user's upper jaw. The upper bite impression channel 36 is manufactured from a relatively soft heat-responsive and impressionable copolymer material such as, for example, ethylene vinyl acetate or a material known commercially as ELVAX No. 150. The upper chassis 38 is manufactured from a relatively hard material such as, for example, polycarbonate or a plastic known commercially as MAKROLON® 2558.

The lower tray assembly 34 of the oral appliance 30 includes a lower bite impression channel 40 and a lower chassis 42 (best shown in FIG. 4) that are molded together so that the lower bite impression channel 40 lies on and is surrounded by the lower chassis 42. Like the upper bite impression channel 36 and the upper chassis 38 of the upper tray assembly 32, the lower bite impression channel 40 and the lower chassis 42 of the lower tray assembly 34 each have a generally arcuate configuration to match the bite pattern of the teeth carried by the user's lower jaw. The lower bite impression channel 40 of the lower tray assembly 34 is preferably manufactured from the same relatively soft and impressionable material as the upper bite impression channel 36 of the upper tray assembly 32, and the lower chassis 42 of the lower tray assembly 34 is preferably manufactured from the same relatively hard material as the upper bite impression channel 36 of the upper tray assembly 32.

The upper bite impression channel 36 of the upper tray assembly 32 is sized to receive therewithin the upper set of teeth of the user carried by his upper jaw. Inasmuch as the relatively soft upper bite impression channel 36 lies on the relatively hard upper chassis 38, a biting force generated by the user's upper set of teeth and applied to the upper bite impression channel 36 can provide the force necessary to shape the upper bite channel 36 in a manner that will soon be described.

The lower bite impression channel 40 of the lower tray assembly 34 is sized to receive therewithin the lower set of teeth of the user carried by his lower jaw. Inasmuch as the relatively soft lower bite impression channel 40 lies on the relatively hard lower chassis 42, a biting force generated by the user's lower set of teeth and applied to the lower bite impression channel 40 can provide the force necessary to shape the lower bite channel 40 from the lower tray assembly 34 at the same time that the upper bite channel 36 from the upper tray assembly 32 is being shaped.

Both the upper bite impression channel 36 of the upper tray assembly 32 and the lower bite impression channel 40 of the lower tray assembly 34 are provided with respective sets 44 and 46 of open cells or holes formed in the impressionable material thereof. By way of a preferred example only, the sets 44 and 46 of holes are arranged in a honeycomb pattern, and each hole has a hexagonal shape. The holes from each of the sets 44 and 46 of holes are uniformly spaced from one another and extend continually around the upper and lower bite impression channels 36 and 40. The sets of holes 44 and 46 are ideally molded into the relatively soft upper and lower bite impression channels 36 and 40 during the manufacture of the upper and lower tray assemblies 32 and 34 of the oral appliance 30. It is to be understood, however, that the particular shape and number of holes from the first and second sets 44 and 46 of holes are not to be considered as a limitation to this invention.

The aforementioned sets 44 and 46 of holes that are formed around the upper and lower bite impression channels 36 and 40 of the upper and lower tray assemblies 32 and 34 advantageously enable a custom fit of the jaw advancement oral appliance 30 in surrounding engagement with the user's upper and lower sets of teeth when the oral appliance is initially prepared for use. That is, and as will be explained in greater detail when the customization and use of the oral appliance 30 are described, the upper and lower tray assemblies 32 and 34 of the oral appliance 30 are first heated and then placed into the user's mouth so that an impression of his teeth will be made when the user bites down and up against the upper and lower bite impression channels 36 and 40 and the sets of holes 44 and 46 formed therein.

A pair of position control pads 48 (only one of which being visible) are located at and molded into opposite sides of the upper tray assembly 32 of the oral appliance 30. A position indication scale 50 is molded into or printed onto each side of the lower tray assembly 34 so as to lie below a position control pad 48. The flexible upper tray assembly 32 is responsive to momentary compressive squeezing forces simultaneously and laterally applied in opposite directions to the position control pads 48 thereof to temporarily compress and change the shape of the upper tray assembly 32 whereby the opposite sides of the upper tray assembly 32 are squeezed towards one another. Although in a preferred embodiment, the compressive squeezing forces are applied to the upper tray assembly 32, it is within the scope of this invention to apply the squeezing forces instead to the lower tray assembly 34 to temporarily compress and change the shape thereof.

The user can now apply a pushing (or pulling) force to slidably relocate and change the position of the lower tray assembly 34 relative to the upper tray assembly 32. In the alternative, the user can also apply a pushing or pulling force to the upper tray assembly 32 to slidably relocate and change the position of the upper tray assembly 32 relative to the lower tray assembly 34. In either case, one of the user's upper or lower jaws will be repositioned relative to the other jaw.

After the position of one of the upper or lower tray assemblies 32 or 34 has been adjusted relative to the other one, the compressive squeezing forces are terminated. Accordingly, the formerly compressed (e.g., upper) tray assembly 32 will automatically expand back to its initial shape so that the upper and lower tray assemblies 32 and 34 are held in place one above the other. The location of the position control pads 48 above the position indication scales 50 provides the user with a visual indication of the position of the lower tray assembly 34 with respect to the upper tray assembly 32 so that the user can make regular controllable and precise position adjustments of the lower tray assembly 34 to correspondingly change the position of his lower jaw relative to his upper jaw and thereby vary the size of the airflow passage 31 to his throat between the upper and lower tray assemblies 32 and 34.

Details of the impression tray 1 which will be used in combination with the aforementioned oral jaw advancement appliance 30 or the like are now described while continuing to refer to FIGS. 1-4. The impression tray 1 includes a rear impression forming stop 3 and front impression forming stop 5 that are detachably connected to one another. In the assembled configuration of the impression tray 1 shown in FIGS. 3 and 4, the rear and front impression forming stops 3 and 5 are spaced from and held opposite one another against the rear and the front of the oral appliance 30. In particular, each of the rear and front impression forming stops 3 and 5 of the impression tray 1 has a curved shape that conforms to the curvature of the upper and lower tray assemblies 32 and 34 of the oral appliance 30.

An elongated straight and flexible (e.g., plastic) handle 7 having a spring memory is integrally connected at a first end thereof to the curved rear impression forming stop 3. A pair of spaced, parallel aligned compression slots 9 run axially along the handle 7. A pair of position locking bumps or projections 10 are located at and extend outwardly from opposite sides of the handle 7. A handle receiving slot 12 is formed through the curved front impression forming stop 5.

The slot 12 is sized to slidably and removably receive therethrough the free end of the handle 7 that lies opposite the first end to which the rear impression forming stop 3 is affixed.

The impression tray 1 is assembled to engage and fit snugly around the curved jaw advancement oral appliance 30 so that the oral appliance can be shaped and customized prior to its first use by the user. To this end, the free end of the handle 7 of the impression tray 1 is inserted and pushed from the back towards the front of the oral appliance 30 for receipt through the air passage 31 between the upper and lower tray assemblies 32 and 34 thereof (best shown in FIG. 4). As the free end of the handle 7 moves through the air passage 31, the position locking bumps 10 that extend from opposite sides of the handle 7 are engaged and pressed in opposite directions inwardly towards the compression slots 9 that run along handle 7.

Squeezing forces are thereby applied to the handle 7 at the position locking bumps 10 thereof. Accordingly, the handle 7 is temporarily compressed into the compression slots 9 so that the width of the handle is narrowed. The handle 7 continues to move through the air passage 31 between the upper and lower tray assemblies 32 and 34 of oral appliance 30 until the curved rear impression forming stop 3 that is fixedly connected to the first end of the handle 7 of the impression tray 1 is pressed into flush engagement against the rear of the curved oral appliance 30 to apply a pressure thereagainst.

At the same time, the position locking bumps 10 are pushed completely through the airflow passage 31 so that the formerly compressed handle 7 of the impression tray 1 will now relax and automatically expand back to its original width. As the position locking bumps 10 exit the airflow passage 31, the handle will function as a spring, whereby the locking bumps 10 are forced away from the compression slots 9 and snapped into locking engagement with the oral appliance 30 against the curved front thereof (best shown in FIG. 3) so as to hold the handle 7 in place and prevent its inadvertent withdrawal from the appliance. Likewise, with the rear impression forming stop 3 lying flush against the rear of the oral appliance 30, the free end of the handle 7 can no longer be moved towards the front of the appliance 30.

With the handle 7 of the impression tray 1 locked in place and the free end of handle 7 extending outwardly from the front of the oral appliance 30, the curved front impression forming stop 5 is now detachably connected to the handle 7. The foregoing is accomplished by moving the front impression forming stop 5 towards the outwardly extending free end of the handle 7. The front impression forming stop 5 is detachably connected to the handle 7 when the free end thereof is pushed through the handle receiving slot 12 formed through the front impression forming stop 5. The front impression forming stop 5 slides continuously along the handle 7 until the stop 5 lies flush against the front of the oral appliance 30 (best shown in FIGS. 3 and 4) to apply a pressure thereagainst. At the same time, the handle 7 is momentarily compressed so that the position locking bumps 10 thereof snap into engagement with and hold the front impression forming stop 5 against the front of oral appliance 30 so as to prevent its sliding off the handle.

Figure 5:
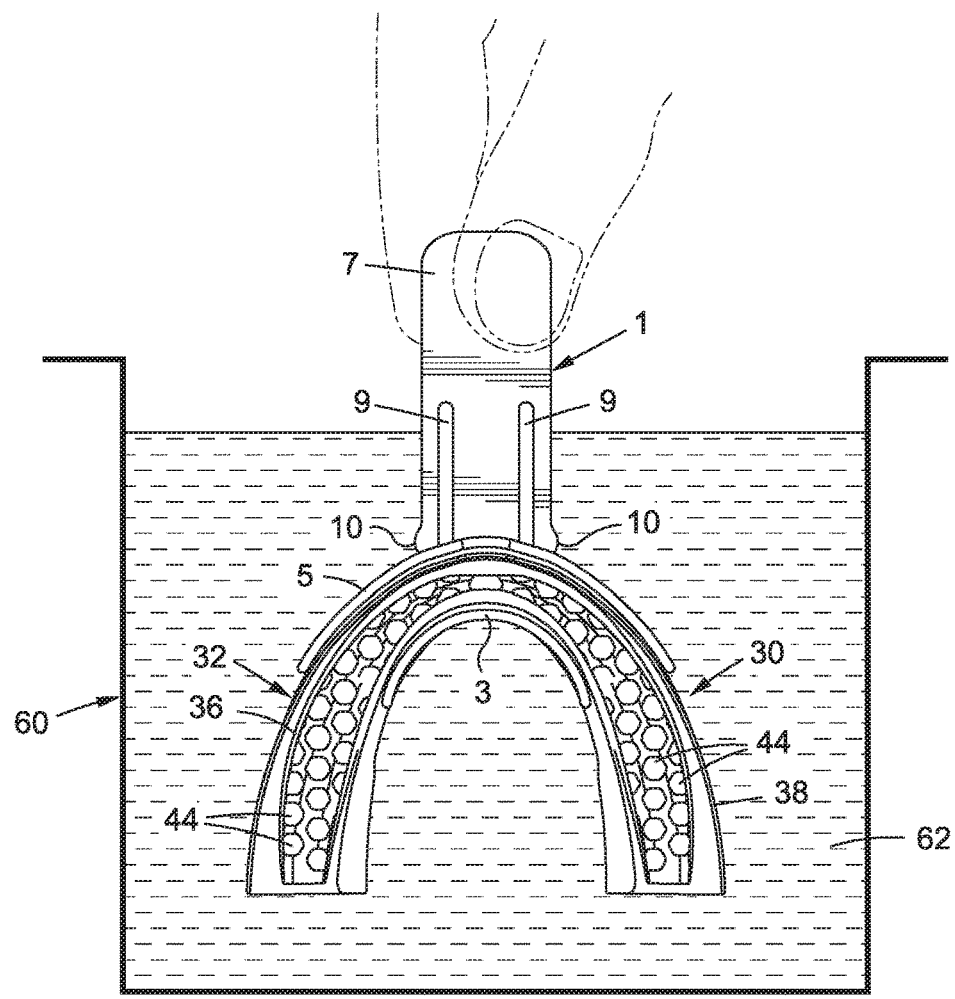
FIG. 5 shows the integral handle of the impression tray being grasped by a user to locate the oral jaw advancement appliance to which the impression tray is removably attached in a pot of boiled water.

As previously explained, prior to its first use, the upper and lower tray assemblies 32 and 34 of the oral jaw advancement appliance 30 are heated and placed into the mouth of the user so that an impression of the user's upper and lower sets of teeth will be made when the user bites on the upper and lower bite impression channels 36 and 40 of the upper and lower tray assemblies 32 and 34. Referring in this regard to FIG. 5 of the drawings, the user is shown gripping the free end of the handle 7 of the impression tray 1 that extends outwardly from the front of the oral appliance 30 and through the front impression forming stop 5 so that the appliance being carried by the impression tray can be lowered into and held within a container 60 of boiled water 62.

Once the oral appliance 30 has been heated for a suitable time (e.g., about 60 seconds), it is lifted out of the container 60 by means of the handle 7 of the impression tray 1. It may be appreciated that the oral appliance 30 is grasped to be inserted and removed from the boiled water 62 by means of the impression tray 1 without the user having to risk burning his hands by using tongs or a similar metal tool as has been used in the past. By virtue of the impression tray 1 described herein, the oral appliance 30 is less likely to be deformed or accidentally dropped into the boiled water. While still warm, the oral appliance 30 is inserted into the user's mouth at which time he closes his mouth and bites on the relatively soft upper bite impression channel 36 and lower bite impression channel 40.

The user's upper set of teeth bite down against the upper bite impression channel 36 of the upper tray assembly 32, and his lower set of teeth bite up against the lower bite impression channel 40 of the lower tray assembly 34. With the rear impression forming stop 3 held flush against the rear of the oral appliance 30 and the front impression forming stop 5 held flush against the front of appliance 30, the impressionable material of the upper and lower bite impression channels 36 and 40 is confined to lying between the opposing impression forming stops 3 and 5 so that a centered and customized impression of the user's upper and lower sets of teeth can be achieved. By virtue of the honeycomb patterns of the sets of holes 44 and 46 and the relatively soft (e.g., copolymer) material of the upper and lower bite impression channels 36 and 40, at least some of the holes from each set thereof will communicate with one another, whereby the impressionable material of the bite impression channels 36 and 40 will be uniformly displaced and flow evenly around the edges and the crevices of the user's teeth. Therefore, accurate impressions of the user's upper and lower sets of teeth are shaped in the opposing bite channels 36 and 40 which lay on and are compressed against the relatively hard upper and lower chassis 38 and 42 of the upper and lower tray assemblies 32 and 34. That is to say, the impressions made in the upper and lower bite impression channels 36 and 40 will closely conform to the shape of the user's teeth to enable the oral appliance 30 will fit snugly around and adhere to the user's teeth so as to be unlikely to shift or fall out of the user's mouth during sleep.

Figure 6:
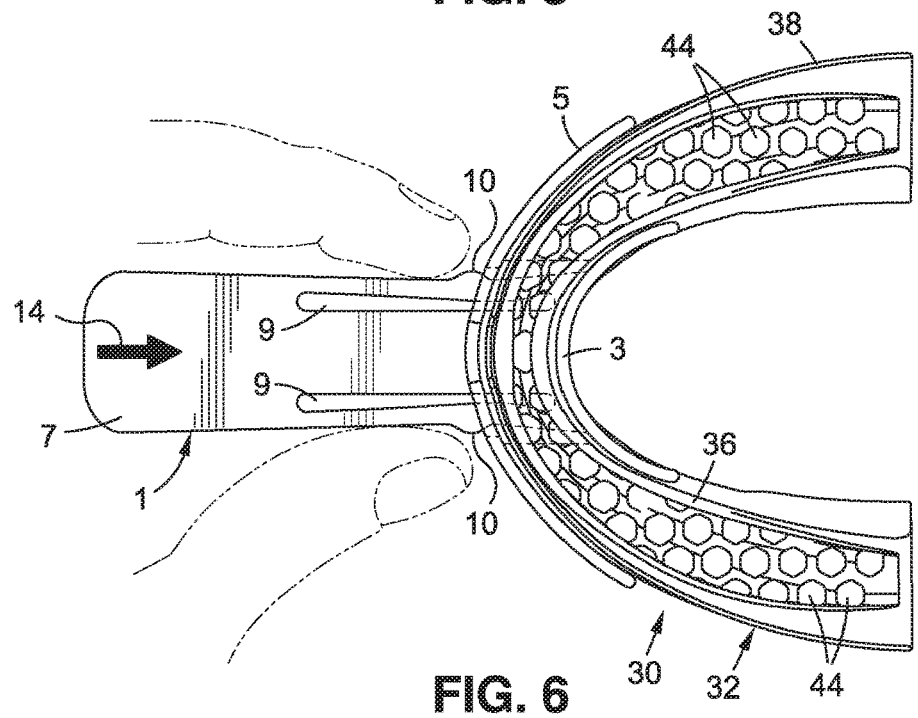
FIG. 6 illustrates the steps for detaching the impression tray from the oral jaw advancement appliance.

After biting on the warm oral jaw advancement appliance 30 for about 30 seconds, the appliance is removed from the user's mouth and placed into a pot of cold water (not shown) where it is cooled. The impression tray 1 is now separated from the oral appliance 30. Referring to FIG. 6 of the drawings, the foregoing is accomplished by once again temporarily squeezing the handle 7 of the impression tray 1. The handle 7 is thusly compressed so that the position locking bumps 10 thereof are moved out of their engagement with the front impression forming stop 5 that has been held against the front of the oral appliance 30. After the front impression forming stop 5 is first pulled off the free end of the handle 7, the handle is then pushed (in the direction of the reference arrow 14) completely through and detached from the appliance 30. The oral appliance 30 is now ready to be used during sleep at which time it is again inserted in the mouth and over the teeth of the user. As previously explained, the appliance 30 is advantageously adapted to position and controllably reposition the patient's lower jaw forward of his upper jaw so that an airway will be maintained to the user's throat so as to reduce the effects of snoring and/or sleep apnea.

The invention claimed is:

1. A combination comprising:

an oral appliance adapted to fit in the mouth and over the teeth of an individual during sleep to maintain an airway to the individual's throat by way of an airflow passage that runs through the oral appliance, said oral appliance having a front and a rear and being formed from an impressionable material that is responsive to heat to enable an impression of the individual's teeth to be made therein, said oral appliance also having a curved configuration that matches the bite pattern of the individual's teeth; and an impression tray removably attached to said oral appliance and adapted to be placed within the mouth of the individual, said impression tray including a handle having first and opposite ends and running completely through said oral appliance by way of the airflow passage thereof so as to extend from the rear of said oral appliance to the front of the said oral appliance, said impression tray also including a rear impression forming stop attached to the first end of said handle and having a curved configuration that matches the curved configuration of said oral appliance so as to lie flush around the rear of said curved oral appliance such that the opposite end of said handle extends from said rear impression forming stop and outwardly from the front of said oral appliance to provide a gripping surface at which said handle is configured to be grasped and said oral appliance is configured to be transported, and a front impression forming stop detachably, connected to the outwardly extending opposite end of said handle and having a curved configuration that also matches the curved configuration of said oral appliance so as to lie flush with and extend continuously and entirely vertically and horizontally around the front of the curved oral appliance, the impressionable material of said oral appliance being confined to lying between said curved front and rear impression forming stops when the impressionable material is heated to make the impression of the individual's teeth.

2. The combination recited in claim 1, further comprising a source of heat, the opposite end of said handle that extends outwardly from the front of said oral appliance is configured to be grasped such that said oral appliance is transportable to said source of heat where the impressionable material of said oral appliance is heated to enable the impression of the individual's teeth to be made therein.

3. The combination recited in claim 1, wherein the front impression forming stop of said impression tray has a handle receiving slot formed therein within which to removably receive therethrough the outwardly extending opposite end of the handle by which said opposite end is detachably connected to said front impression forming stop.

4. The combination recited in claim 1, wherein the handle of said impression tray has a spring memory and at least one compression slot formed therein and running axially therealong at which said handle is compressed in response to squeezing forces applied to opposite sides thereof.

5. The combination recited m claim 4, wherein the handle of said impression tray also has a position locking bump located at each of the opposite sides thereof and moving towards one another and towards said at least one compression slot when said handle is compressed, said position locking humps moving away from one another and into engagement with the front impression forming stop at the front of the oral appliance to hold said front impression forming stop flush against the front of said oral appliance when the squeezing forces applied to the opposite sides of said handle are terminated and said handle expands.

6. A method for making an impression of the teeth of an individual in an oral appliance having a front and back so that the oral appliance can fit in the mouth and over the teeth of the individual to maintain an airway to the individual's throat by way of an airflow passage that runs through the oral appliance, said method comprising the steps of:

removably attaching an impression tray to said oral appliance and adapted to be placed within the mouth of the individual, said oral appliance being made from a heat responsive impressionable material and having a curved configuration that matches the bite pattern of the individual's teeth, said impression tray including a handle having first and opposite ends;

attaching to the first end of said handle a rear impression forming stop having a curved configuration that matches the curved configuration of said oral appliance and pushing said rear impression forming stop against the back of said oral appliance such that the curved rear impression forming stop lies flush around the back of the oral appliance and the opposite end of said handle moves through the airflow passage of said oral appliance and extends outwardly from the front of said oral appliance to establish a gripping surface at which said handle is grasped and said oral appliance is transported;

detachably connecting to the outwardly extending opposite end of said handle a front impression forming stop having a curved configuration that also matches the curved configuration of said oral appliance and moving said front impression forming stop along said handle until said curved front impression forming stop lies flush with and extends continuously and entirely vertically and horizontally around the front of said oral appliance;

grasping the outwardly extending opposite end of the handle of said impression tray and transporting said oral appliance to a source of heat;

heating said oral appliance;

grasping the outwardly extending opposite end of the handle of said impression tray after said oral appliance has been heated, and moving the heated oral appliance from the source of heat into the mouth of the individual to enable the individual to bite into said oral appliance such that the impressionable material of said oral appliance is confined to lying between said curved front and rear impression forming stops, whereby the impression of the individual's teeth is made; and removing the oral appliance from the mouth of the individual and detaching the impression tray therefrom.

* * * * *